United States Patent
Sasik et al.

(10) Patent No.: US 9,034,305 B1
(45) Date of Patent: May 19, 2015

(54) AQUEOUS HAIR STYLING COMPOSITIONS COMPRISING TWO ACRYLATE SILICONE COPOLYMERS

(71) Applicant: ELC Management LLC, Melville, NY (US)

(72) Inventors: Camille Sasik, Minnetonka, MN (US); Jean Harry Xavier, Stony Brook, NY (US); Geoffrey Hawkins, Yardley, PA (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 14/192,914

(22) Filed: Feb. 28, 2014

(51) Int. Cl.
| | |
|---|---|
| *A61Q 5/06* | (2006.01) |
| *A61Q 5/12* | (2006.01) |
| *A61K 8/891* | (2006.01) |
| *A61K 8/81* | (2006.01) |
| *A61Q 5/02* | (2006.01) |
| *A45D 7/06* | (2006.01) |

(52) U.S. Cl.
CPC .............. *A61K 8/891* (2013.01); *A61K 8/8147* (2013.01); *A61Q 5/06* (2013.01); *A61Q 5/02* (2013.01); *A61Q 5/12* (2013.01); *A45D 7/06* (2013.01); *A61K 2800/30* (2013.01); *A61K 2800/48* (2013.01); *A61K 2800/596* (2013.01); *A61K 2800/594* (2013.01)

(58) Field of Classification Search
CPC ............ A61K 8/891; A61Q 5/06; A61Q 5/12
See application file for complete search history.

(56) References Cited

U.S. PATENT DOCUMENTS

| | | |
|---|---|---|
| 5,730,966 A | 3/1998 | Torgerson et al. |
| 5,916,547 A | 6/1999 | Torgerson et al. |
| 6,074,628 A | 6/2000 | Bolich, Jr. et al. |
| 6,165,455 A | 12/2000 | Torgerson et al. |
| 6,207,782 B1 | 3/2001 | Czech et al. |
| 6,537,532 B1 | 3/2003 | Torgerson et al. |
| 2010/0047202 A1* | 2/2010 | Goddinger et al. ........ 424/70.12 |

* cited by examiner

*Primary Examiner* — Tigabu Kassa
(74) *Attorney, Agent, or Firm* — Peter Giancana (57) ABSTRACT

A water-based hair styling composition that is easy to make, and that provides excellent flexibility and hold with a natural appearance. The compositions utilize a flexible polymer system that comprises acrylates/dimethicone copolymer and dimethicone PEG-8 polyacrylate in specified ratios.

7 Claims, 4 Drawing Sheets

AQUEOUS HAIR STYLING COMPOSITIONS COMPRISING TWO ACRYLATE SILICONE COPOLYMERS

FIELD OF THE INVENTION

The present invention relates to compositions for hair setting and styling.

BACKGROUND OF THE INVENTION

Many commercial hair styling products in form of sprays, lotions, gels, and mousses, use resins or gums to provide long term hold of up to several hours. However, gums and resins in hair styling products make the hair sticky and stiff, with an unnatural appearance, and are difficult to wash out. In search of a balance between hold and flexibility, some have turned to thermoplastic elastomeric copolymers, which provide measures of hold and flexibility, with a more natural appearance. In general, however, thermoplastic elastomeric copolymers are difficult to incorporate into shampoo and conditioner products, due to their low solubility into water and alcohol. To address the low solubility issue specific copolymer systems have been proposed.

U.S. Pat. Nos. 6,537,532 and 5,916,547 (Torgerson, et. al.) disclose triblock copolymer systems, ABC. The 'A' block is a thermoplastic elastomer that softens upon heating, but exhibits resistance to deformation at room temperature and below. The 'A' block acts as a backbone of the subject copolymers, and is made of polymerizable, ethylenically unsaturated monomer, such as acrylic acid, salts, esters and amides thereof. A 'B' block is a hydrophilic macromonomer unit of polyethylene glycol-type polymer. 'B' units are arranged as side chains on the 'A' backbone. As thermoplastic elastomers typically have low water solubility, the presence of the 'B' block side chains has the benefit of increasing the water solubility of the copolymer system. The 'C' block units are polysiloxane macromonomers, also arranged as side chains on the 'A' backbone. It is reported that the triblock copolymer systems display at least two distinct glass transition temperatures, one for the backbone and polysiloxane side chains, (about −130° C. to −10° C.), and one for the hydrophilic side chains (greater than room temperature, i.e. >20-25° C.). Because the copolymers are typically used at temperatures above the glass transition temperature of the backbone and polysiloxane side chains, the copolymers maintain a degree of flexibility. On the other hand, at room temperature, which is below the glass transition temperature of the hydrophilic side chains, the copolymers will have a degree of structural rigidity from these hydrophilic side chains. The copolymers are said to be water and alcohol soluble or dispersible, and are appropriate for use in hair care applications, where a strong, yet flexible hold for style retention is desired, along with a smooth feel and shine.

U.S. Pat. No. 5,730,966 (Torgerson, et. al) discloses water or alcohol soluble thermoplastic elastomeric copolymers having two or more polymeric pendant side chains. The copolymer is formed from the copolymerization of randomly repeating A and B units, where 'A' is a monomer and 'B' is a hydrophilic macromonomer. The copolymer has an average molecular weight greater than 10,000 Daltons, and has two distinct glass transition temperatures; one less than 0° C. and one greater than 25° C. The copolymers are incorporated into hair and/or skin care applications.

U.S. Pat. No. 6,165,455 (Torgerson, et. al) discloses hair care compositions containing nonpolar graft thermoplastic elastomeric copolymers and a water insoluble volatile solvent for the copolymers. In this case a thermoplastic elastomeric backbone is grafted with hydrophobic and polysiloxane macromonomers to form an ABC copolymer.

U.S. Pat. No. 6,074,628 (Bolich, Jr., et. al) discloses hairspray compositions with an alcohol solvent and a silicone-containing adhesive block copolymer. The block copolymers are either A-B, A-B-A or -(A-B)n- type structures. It is reported that the alcohol solvents, combined with the select silicone-containing adhesive block polymers were effective at providing improved hair styling performance, specifically minimizing or eliminating the undesirable drooping of dry, styled or positioned hair.

These and other hair styling compositions rely on a silicone grafted block copolymers that are relatively hard to make and/or expensive to purchase. None of the foregoing references discloses two specific types of acrylate silicone copolymers mixed in the well defined ratios disclosed herein. The present invention identifies well defined mixtures of two specific types of acrylate silicone copolymers for use in easy-to-formulate hair care products. The acrylate silicone copolymers are water dispersible. The aqueous shampoos and conditioners that comprise these two copolymers as their exclusive or main hair styling ingredients offer hair styling and hold benefits that are at least as good as commercially available hair styling products, albeit with a more natural appearance. These benefits are achievable even when the product is implemented as a rinse-out product.

Objectives

The main objective of the present invention is a water-based hair styling composition that is easy to make, and that provides excellent flexibility and hold with a natural (i.e. not overly stiff) appearance.

Another objective is to provide a flexible polymer system that, when incorporated into a rinse-our product (i.e. a shampoo or conditioner), offers flexibility and hold that are comparable to leave-in hair styling products with gums and resins.

DETAILED DESCRIPTION

In preferred hair styling compositions according to the present invention, two types of acrylate silicone copolymers are mixed in well defined ratios. In normal environments, where you want a composition of the present invention to supply strong hold to styled hair, the hair will generally be exposed to temperatures between about 0° C. and 40° C. On the other hand, during hair styling (when you want the composition to flow more easily) the hair may be exposed to temperatures as high as 175° C. Thus, the two copolymer system of the present invention should exhibit multiple glass transitions temperatures, of which the highest and lowest may be designated as "high $T_g$" and "low $T_g$". High $T_g$ should be well above 40° C. However, if a copolymer with high $T_g$ greater than about 60° C. is used, then compositions of the invention may exhibit a brittle quality, which leads to less than satisfactory results in hair styling. Therefore, it is preferable if high $T_g=50°$ C.-60° C. Low $T_g$ should be below 0° C.

When the treated hair is subjected to temperatures near or above high $T_g$, then all portions of the two copolymer system are softened and flow more easily, which greatly facilitates hair styling. On the other hand, at normal temperatures (0° C. to 40° C.), the high $T_g$ portions of the two copolymer system will stiffen to provide hold to the hair, while the low $T_g$ portions of the two copolymer system will maintain a degree of flexibility. This feature will ensure that compositions of the invention provide both a degree of structural rigidity and a degree of flexibility in styled hair.

The first copolymer may be represented by the following formula.

The repeating unit comprises an acrylate portion (—CH$_2$—CHCO—) attached to a PEG-8 portion ([OC$_2$H$_4$]$_8$O), and between two of those, is sandwiched a polysiloxane (silicone) portion (i.e. a polymer containing repeating silicon-oxygen bonds). A preferred silicone portion is dimethicone. To increase effectiveness, this copolymer should be hydrophilic, preferably having a water contact angle of less than 70°, more preferably less than 50°; a viscosity in the approximate range of <1,000 cst at 25° C.; and be electrically neutral. A preferred copolymer of this type is Dimethicone PEG-8 Polyacrylate (INCI name). Dimethicone PEG-8 Polyacrylate has a $T_g$ that is below 0° C.

The second acrylate silicone copolymer may be represented as an acrylate backbone having silicone side chains:

The polyacrylate portion imparts hardness and heat stability to the copolymer. Typically, the copolymer may comprise 15,000-30,000 Da of acrylate. Furthermore, to increase effectiveness of compositions according to the present invention, this copolymer should preferably be hydrophobic, preferably having a water contact angle of at least 100°, more preferably at least 120°; a viscosity in the approximate range of 500 to 5,000 cst; and be electrically neutral. Preferably, the silicone is also present in the copolymer at a level that imparts a smooth feel to the hair. To these ends, the copolymer preferably comprises 15,000±20% Da of silicone. The silicone side chains provide the water repellency and smoothness, which is a significant added benefit. Preferred, is an acrylate backbone with side chains of dimethicone (i.e. Acrylates/Dimethicone copolymer). The acrylic backbone has a $T_g$ of about 50° C., while the dimethicone side chains may have a Tg<0° C.

Thus, a two copolymer system comprising Dimethicone PEG-8 Polyacrylate and Acrylates/Dimethicone copolymer, has a high $T_g$ of about 50° C., and a low $T_g$ that is below 0° C. Unexpectedly, we have noted that the performance of water based hair care products that comprise these two copolymers as their exclusive or main hair styling ingredients, are quite sensitive to the ratio of the two copolymers, and that the ratio can be optimized to provide an effective rinse-out hair styling product.

To determine the best concentrations of the acrylate silicone copolymers, we prepared rinse-out compositions, specifically, shampoo and conditioner products, that incorporated varying amounts of the hydrophilic copolymer dimethicone/PEG-8 acrylate, and the hydrophobic copolymer acrylates/dimethicone. To assess their ability to impart and retain curl, these shampoos and conditioners were subjected to the following test protocol.

Test Procedure

Except where noted, curl retention over time was measured according to the following protocol.

1. Hair tresses of 3.0 g were provided as test samples.
2. Prior to treatment, the length of each fully extended tress of hair was measured.
3. Tresses were wetted, and a fixed amount of test product (0.3 g) was applied to each tress of hair, and lathered on the hair.
4. The product was allowed to remain on the hair for two to three minutes. Thereafter, excess product was rinsed out of the hair with water.
5. Each tress was heat styled (for example, with a curling iron at about 98° C.) for up to one minute to impart curl.
6. Once curled, some samples were exposed to ambient conditions (temperature=25° C., relative humidity=40-45%), and some samples were exposed to high humidity conditions (temperature=25° C., relative humidity=85-90%) for several hours.
7. At various times, the curl length was measured, and the following curl retention calculation of was made:

% Curl Retention=$(L_t-L_f)/(L_t-L_i)\times 100$, where $L_t$ length of fully extended tress prior to treatment
$L_f$ length of curled tress at measurement time
$L_i$ length of curled tress at time t=0 (i.e. immediately after curling treatment)

8. Each test sample was also evaluated for aesthetic considerations (i.e. is the appearance natural? is there a visible residue on the hair? is the hair soft and smooth?).

The tested products included controls, comparative commercial products, and compositions according to the present invention with various levels and ratios of the two types of acrylate silicone copolymers described above. In each of the tests described below and in the corresponding figures, sample labels 1a and 1b refer to test formula 1 maintained at low humidity, and test formula 1 maintained at high humidity, respectively; sample labels 2a and 2b refer to test formula 2 maintained at low humidity, and test formula 2 maintained at high humidity, respectively; and so on.

Throughout the test examples, the test compositions were prepared with commercially available forms of Acrylates/Dimethicone and Dimethicone PEG-8 Polyacrylate. The materials used were: KP-549 (available from Shin-Etsu), which is 40% acrylates/dimethicone copolymer in a methyl trimethicone diluent; and Silsoft Surface PF (available from Momentive Performance Materials) which is 21.86% Dimethicone PEG-8 Polyacrylate in a silicone-in-water emulsion. These materials were added to the base compositions such that the concentrations of Acrylates/Dimethicone and Dimethicone PEG-8 Polyacrylate were as shown.

Test Example 1 A base shampoo composition, which was used for the control samples, was prepared according to following formula:

| CTFA Name | Wt % |
| --- | --- |
| Water | q.s. |
| Xanthan gum | 1.20 |
| Ammonium lauryl sulfate | 38.00 |
| Cocamide MIPA | 2.00 |
| Glycol distearate | 1.00 |
| Citric acid | 0.10 |
| Methylchloroisothiazolinone/ Methylisothiazolinone | 0.16 |

Test compositions were prepared by dispersing into the base formula various amounts of Acrylates/Dimethicone and Dimethicone PEG-8 Polyacrylate. Control and test samples were prepared by applying the compositions to hair tresses, as follows:

| Test Formula | Acrylates/ Dimethicone | Dimethicone PEG-8 Polyacrylate | Ratio |
| --- | --- | --- | --- |
| 1 | 1.00% | 0.44% | 2.27:1 |
| 2 | 2.00% | 0.66% | 3.03:1 |
| 3 | 2.72% | 0.66% | 4.12:1 |
| 4 | 3.20% | 0.66% | 4.85:1 |

Figure 1A:
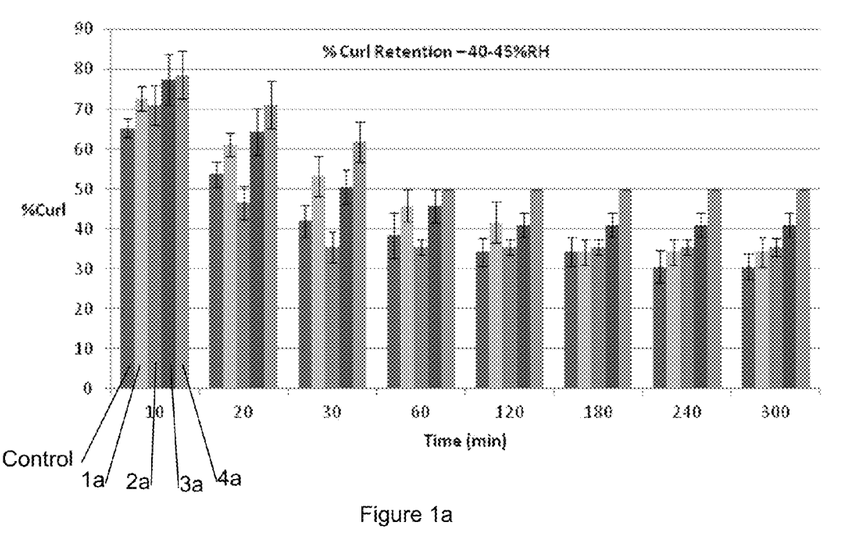
FIGS. 1a, 1b depict results of a curl retention test for a shampoo according to the present invention.
Figure 1B:
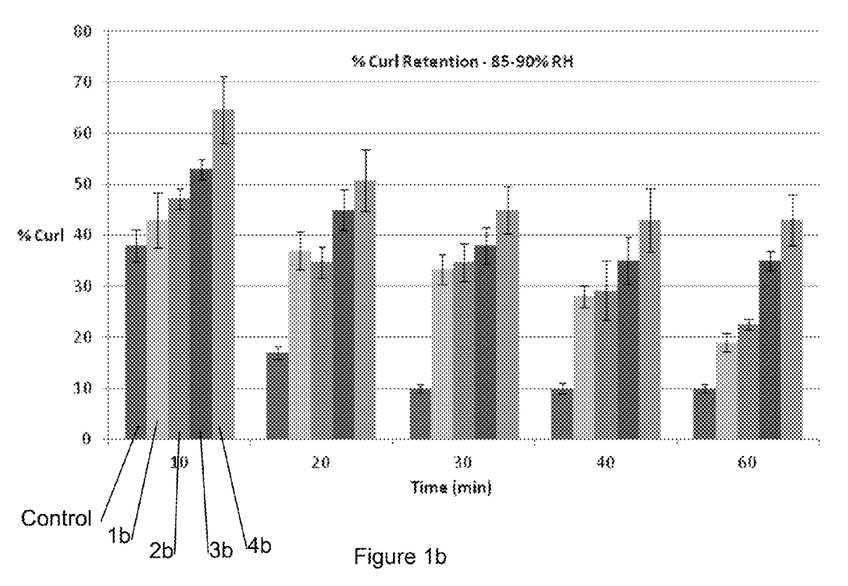

Testing was carried out according to the protocol described above.
Results (Refer to FIGS. 1a and 1b)
At 40-45% relative humidity, test samples 1a, 3a and 4a retained curl better than the control sample, over the life of the test. Test sample 2a performed better than the control in the second half of the test. At 85-90% RH, the results were even more dramatic. All four test samples retained curl significantly better than the control over the life of the test. Overall, test formula 4 retained curl the best (50% curl retention after 5 hours at low humidity, and 43% curl retention after 1 hour at high humidity, compared to 30.6% and 10% for the control). Next best was test formula 3, and then test formulae 1 and 2, which performed similarly to each other.
Discussion and Conclusion
In this test example, a ratio of about 4.85:1 is preferred, although ratios as low as 2.3:1 still gives a useful result. Overall, a topical hair composition comprising Acrylates/Dimethicone Copolymer and Dimethicone PEG-8 Polyacrylate in ratios of about 2:1 to 5:1, as the only or main curl retention agents, are useful for retaining curl in styled hair.

Test Example 2 A base hair conditioner composition, which was used for the control samples, was prepared according to following formula:

| CTFA Name | Wt % |
| --- | --- |
| Water | q.s. |
| Polyquaternium-4 | 0.85 |
| Hydroxyethylcellulose | 0.50 |
| Citric acid | 0.13 |
| Methylchloroisothiazolinone/ Methylisothiazolinone | 0.04 |
| Sodium chloride | 0.01 |
| Cetyl alcohol | 1.00 |
| Stearyl alcohol | 0.70 |
| Ceteareth-20 | 0.35 |

Test compositions were prepared by dispersing into the base formula various amounts of Acrylates/Dimethicone and Dimethicone PEG-8 Polyacrylate. Control and test samples were prepared by applying the compositions to hair tresses, as follows:

| Test Formula | Acrylates/ Dimethicone | Dimethicone PEG-8 Polyacrylate | Ratio |
| --- | --- | --- | --- |
| 1 | 5.00% | 0.66% | 7.58:1 |
| 2 | 3.00% | 0.66% | 4.55:1 |
| 3 | 4.00% | 0.66% | 6.06:1 |
| 4 | 4.00% | 0.44% | 9.09:1 |
| 5 | 4.00% | 0.22% | 18.18:1 |

Figure 2A:
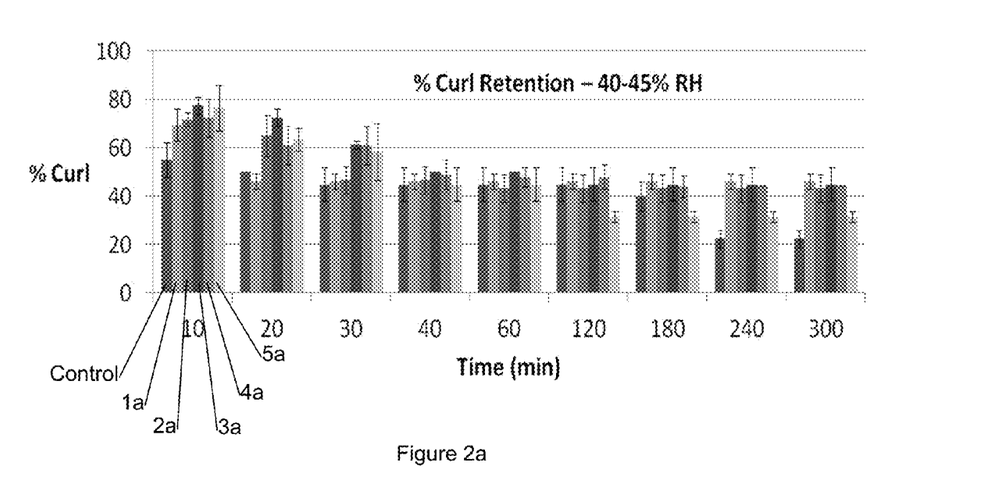
FIGS. 2a, 2b depict results of a curl retention test for a conditioner according to the present invention.
Figure 2B:
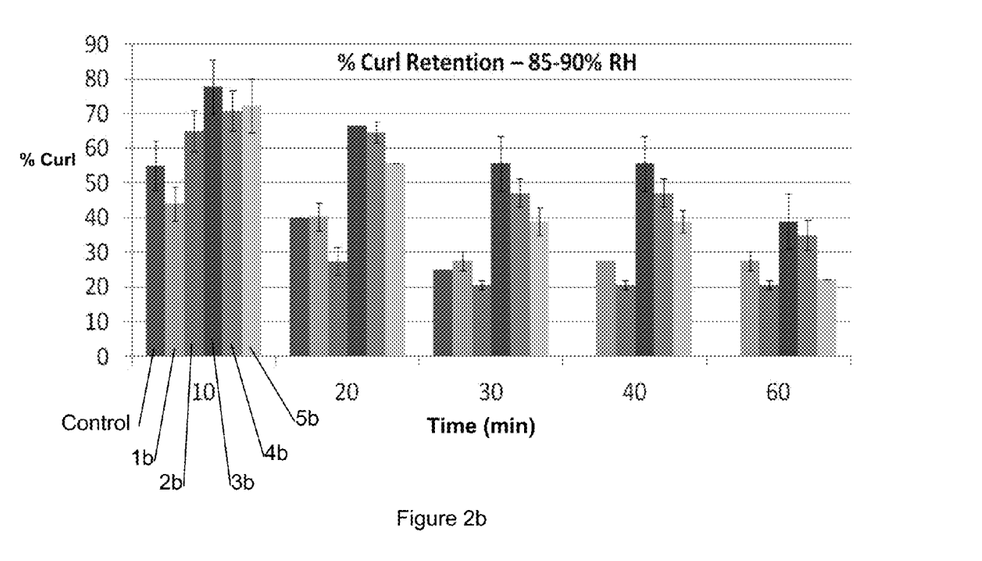

The control and test compositions were applied to the hair tresses and tested according to the protocol described above.
Results (Refer to FIGS. 2a and 2b)
At 40-45% relative humidity, test formulae 3 and 4 retained curl better than the control sample, over the life of the test. Test formulae 1, 2 and 5 gave mixed results compared to the control. At 85-90% RH, test formulas 3, 4 and 5 retained curl significantly better than the control, over the life of the test, while formulae 1 and 2 performed better than the control in the second half of the test. Overall, test formulae 3 and 4 retained curl the best (45% and 44.4% after 5 hours at low humidity, and 38.9% and 35%, after 1 hour at high humidity, compared to 22.5% and 0% for the control). Next best were test formula 1, then formula 5, and then formula 2.
Discussion and Conclusion
In this test example, a ratio of about 6:1 to 9:1 is preferred, although a ratio as low as about 4.5:1 and as high as 18:1 still gives a useful result, especially for high humidity environments. Overall, a rinse-out hair composition comprising Acrylates/Dimethicone Copolymer and Dimethicone PEG-8 Polyacrylate in ratios of about 4.5:1 to 18:1, as the only or main curl retention agents, are useful for retaining curl in styled hair.

Test Examples 3 and 4 A wash-out shampoo composition and a wash-out conditioner composition were prepared according to the following formulae:

| Shampoo | Wt % |
| --- | --- |
| Water | Q.S. |
| Cocamide MIPA | 5.00 |
| Carrageenan | 1.00 |
| Glycol distearate | 1.00 |
| Ammonium lauryl sulfate | 20.0 |
| Coco betaine | 5.00 |
| Fragrance | 0.40 |
| Methyl Chloroisothiazolinone/ methylisothozolinone | 0.05 |
| Phenoxyethanol | 0.70 |
| Silsoft Surface PF* | 3.00 |
| KP-549** | 12.5 |
| Citric acid | 0.05 |

| Conditioner | Wt % |
| --- | --- |
| Water | Q.S. |
| Polyquaternium-4 | 0.85 |
| Hydroxyethylcellulose | 0.50 |
| Citric acid | 0.13 |
| Methylchloroisothiazolinone/ Methyl isothiazolinone | 0.40 |
| Sodium chloride | 0.01 |
| Cetyl alcohol | 1.00 |
| Stearyl alcohol | 0.70 |
| Ceteareth-20 | 0.35 |
| Silsoft Surface PF* | 3.00 |
| KP-549** | 10.0 |

-continued

Test Examples 3 and 4 A wash-out shampoo composition and a wash-out conditioner composition were prepared according to the following formulae:

*21.86% Dimethicone PEG-8 Polyacrylate (Momentive Performance Materials)
**40% Acrylates / Dimethicone Copolymer in trimethicone (Shin-Etsu Chem. Co.)

The test shampoo (formula 5) and test conditioner (formula 6) according to the present invention were applied to hair tresses and tested according to the protocol described above. For comparison, test samples were also prepared with the following commercially available leave-in products: Bumble & bumble Gel (formula 1), Bumble & bumble Lotion (formula 2), Bumble & bumble Thickening Spray (formula 3), Bumble & bumble Thickening Mousse (formula 4). For these test samples, 0.3 grams of the leave-in product was applied to hair tresses as per product instructions, and remained in the hair throughout testing (i.e. the tresses were not rinsed after product was applied).

Figure 3A:
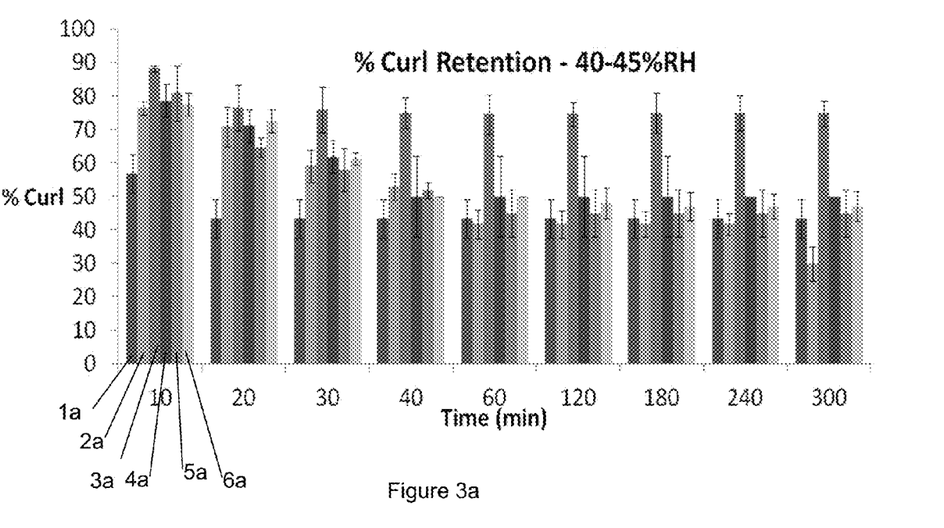
FIGS. 3a, 3b depict results of a curl retention test for a shampoo and a conditioner according to the present invention, compared to several commercial products.
Figure 3B:
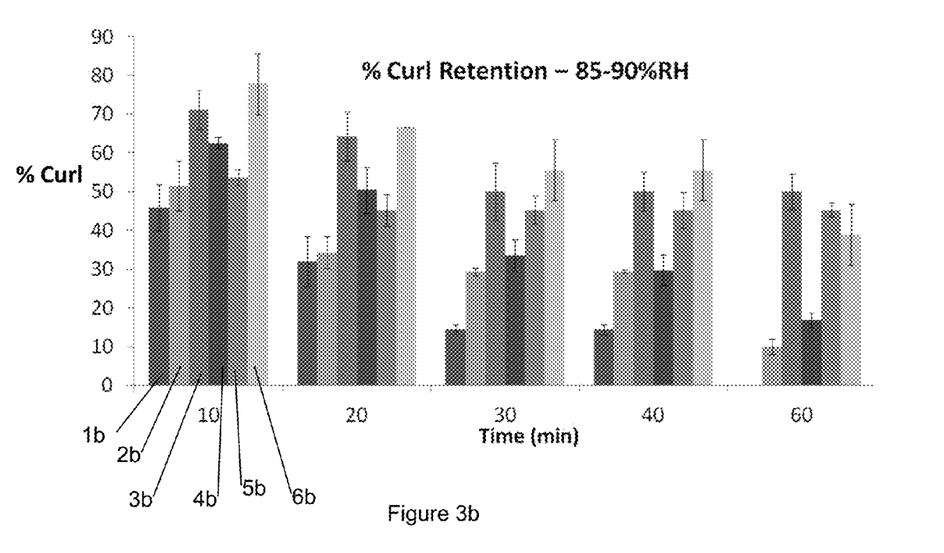

Results (Refer to FIGS. 3a and 3b)

At 40-45% relative humidity for 5 hours, the shampoo sample (5a) and conditioner sample (6a) according to the above formulae retained curl significantly better (45% and 47%, respectively) than Bumble & bumble Lotion (29.9%). The shampoo and conditioner retained curl about as well as Bumble & bumble Gel and Bumble & bumble Thickening Mousse, but not as well as Bumble & bumble Thickening Spray (74.8%).

At 85-90% relative humidity for 1 hour, the shampoo sample (5b) and conditioner sample (6b) according to the above formulae retained curl significantly better (about 45.2% and 38.9%, respectively) than Bumble & bumble Gel (0%), Bumble & bumble Lotion (10%) and Bumble & bumble Thickening Mousse (about 16.8%). The shampoo retained curl about as well as Bumble & bumble Thickening Spray (50%), which performed only slight better than the conditioner.

Discussion and Conclusion

The shampoo comprised 5.0% Acrylates/Dimethicone Copolymer and 0.66% Dimethicone PEG-8 Polyacrylate (a ratio of 7.6:1). The conditioner in this example comprised 4.0% Acrylates/Dimethicone Copolymer and 0.66% Dimethicone PEG-8 Polyacrylate (a ratio of 6:1). In this test example, two rinse-out hair compositions comprising Acrylates/Dimethicone Copolymer and Dimethicone PEG-8 Polyacrylate in ratios of about 6:1 to 7.6:1, as the only or main curl retention agents, were able to retain curl better than or as well as several leave-in commercial hair styling products.

Test Example 5 A base shampoo composition which acted as the test control, was prepared according to following formula:

| INCI Name | Wt % |
| --- | --- |
| Water | q.s. |
| Cocamide MIPA | 5.00 |
| Ammonium Lauryl Sulfate | 20.00 |
| Carrageenan Extract | 0.70 |
| Carrageenan Extract | 0.30 |
| Glycol Distearate | 1.00 |

Test compositions were prepared by dispersing into the base formula various amounts of Acrylates/Dimethicone and Dimethicone PEG-8 Polyacrylate, as follows:

| Test Sample ID # | Acrylates/ Dimethicone | Dimethicone PEG-8 Polyacrylate | Ratio |
| --- | --- | --- | --- |
| 1a,b | 3.00% | 0.66% | 4.6:1 |
| 2a,b | 4.00% | 0.66% | 6.1:1 |
| 3a,b | 5.00% | 0.66% | 7.6:1 |
| 4a,b | 5.00% | 0.44% | 11.4:1 |
| 5a,b | 5.00% | 0.22% | 22.7:1 |

The control and test compositions were applied to the hair tresses and tested according to the protocol described above.

Figure 4A:
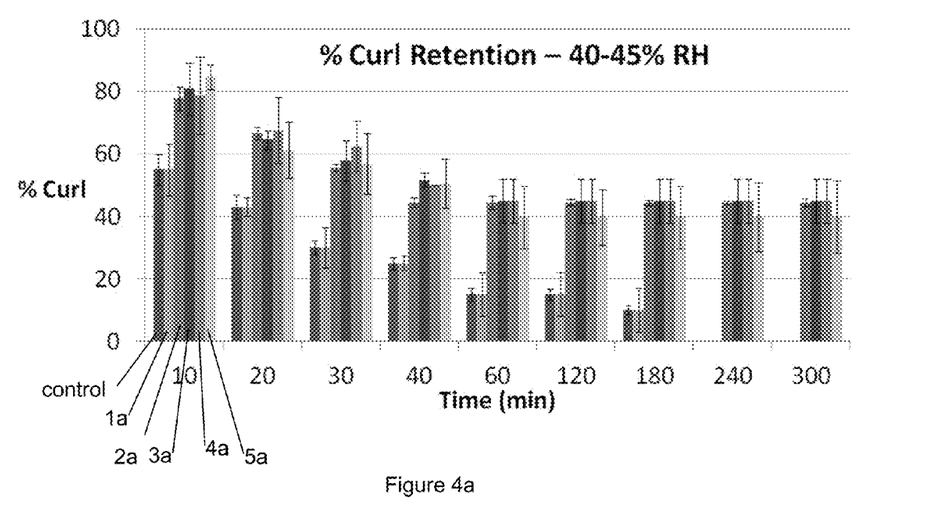
FIGS. 4a, 4b depict results of a curl retention test for a shampoo according to the present invention.
Figure 4B:
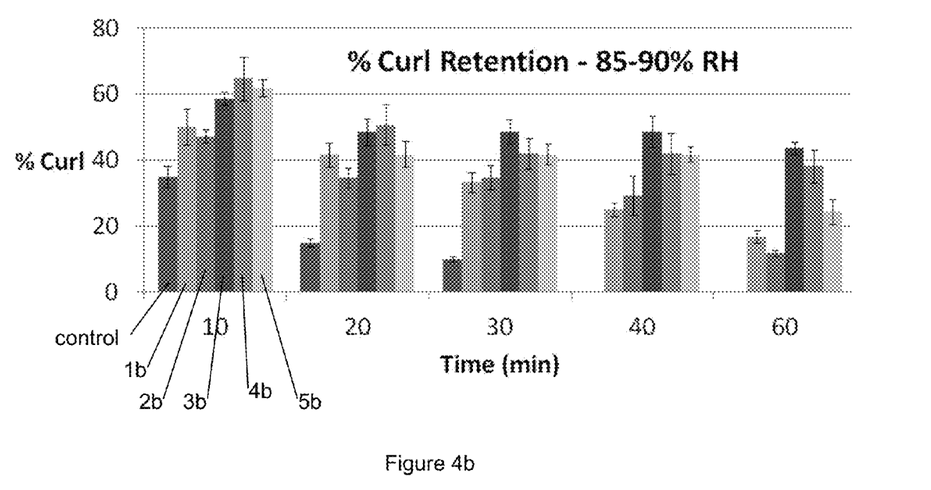

Results (Refer to FIGS. 4a and 4b)

At 45-45% relative humidity, test formula 1 performed comparably to the control sample, throughout the test period, while test formulae 2-5 significantly outperformed the control sample. Test formula 5a did not perform as well as test formulae 2-4, and test formulae 3 and 4 performed slightly better than test formula 2. At 85-90% relative humidity, test formulae 1-5 significantly outperformed the control sample throughout the test period. Overall, test formula 3 performed best, followed by test formulae 4, 5, 1 and 2 in order of decreasing performance.

Discussion and Conclusions

At either level of humidity, test formulae 3 and 4 provided superior curl retention (45% at low humidity for 5 hours, and 43.6% and 38.1% respectively, at high humidity for 1 hour) compared to the control which offered 0% curl retention before the end of either test period. Furthermore, test formulae 2 and 5 outperformed the control at either level of humidity.

This test example suggests that rinse-out compositions comprising acrylates/dimethicone copolymer and dimethicone PEG-8 polyacrylate as the only or main curl retention agents, are effective to retain curl when used in a ratio of about 6.1:1 to 22.7:1, while a ratio of about 7.6:1 to 11.4:1 is more preferred.

Overall Conclusions on Test Examples 1-5

Rinse-out compositions comprising acrylates/dimethicone copolymer and dimethicone PEG-8 polyacrylate as the only or main curl retention agents, are effective to retain curl when used in a ratio of about 2:1 to 23:1. A ratio of about 4:1 to 18:1 is preferred, while a ratio of about 6:1 to 9:1 is most preferred. Typical concentrations of the two polymers are 0.5 to 5 wt. % (acrylates/dimethicone copolymer) and 0.1 to 1 wt. % (dimethicone PEG-8 polyacrylate). Below these levels leads to less effective hold, especially when the acrylates/dimethicone copolymer and dimethicone PEG-8 polyacrylate are the only styling hold agents in the composition. Above these levels can lead an excessive amount of residue that remains in the hair after normal rinsing, to the point that is becomes visible and perhaps heavy. However, within the ranges specified, excellent stylability and hold are achieved with rinse-out type products. The substantivity of the hair for acrylates/dimethicone copolymer and dimethicone PEG-8 polyacrylate are sufficient to achieve unexpectedly good results. The hold is at least as good as many leave-in commercial styling products, without the stiff look and heavy feel, and without the greasy look and feel of so many hair styling products. In fact, the dimethicone side chains of the Acrylates/Dimethicone copolymer provide the additional advantages of smoothness and water repellency.

Furthermore, while compositions of the present invention provide excellent hair styling hold, the hair maintains a significant degree of flexibility due to the high and low glass transition temperatures of the composition, especially when the acrylates/dimethicone copolymer and dimethicone PEG-8 polyacrylate are the only styling hold agents in the composition. Also, the objective of a styling system that is easily dispersed in water systems has been achieved, as demonstrated by the following examples and procedures.

Product Example 1 - Hair Styling Shampoo

| | wt. % | |
|---|---|---|
| (1) | 55.7 | Water |
| (1) | 5.0 | Cocamide MIPA |
| (1) | 1.0 | Carrageenan |
| (1) | 1.0 | Glycol Distearate |
| (2) | 20.0 | Ammonium Lauryl Sulfate |
| (2) | 5.0 | Cocobetaine |
| (3) | 0.1 | Citric acid |
| (4) | 2.30 | Silsoft Surface PF * |
| (4) | 8.75 | KP-549 ** |
| (5) | 0.4 | Fragrance |
| (5) | 0.05 | Methyl chloroisothiazolinone / methylisothozolinone |
| (5) | 0.7 | Phenoxyethanol |

* 21.86% Dimethicone PEG-8 Polyacrylate (Momentive Performance Materials)
** 40% Acrylates / Dimethicone Copolymer in trimethicone (Shin-Etsu Chem. Co.)

to a main kettle, add phase 1, and heat to 80° C.;
add phase 2, and cool to 60° C.;
at 60° C., add phases 3 and 4;
at <40° C., add phase 5;
adjust to ph=4.5;

Product Example 2 - Hair Styling Conditioner

| | wt. % | |
|---|---|---|
| (1) | 80.49 | Water |
| (1) | 0.9 | Polyquaternium -4 |
| (1) | 0.5 | Hydroxyethyl cellulose |
| (1) | 0.13 | Citric acid |
| (1) | 0.01 | Sodium Chloride |
| (2) | 1.0 | Cetyl alcohol |
| (2) | 0.7 | Stearyl alcohol |
| (2) | 0.35 | Cetereath -20 |
| (3) | 2.86 | Silsoft Surface PF * |
| (3) | 12.5 | KP-549 ** |
| (4) | 0.4 | Fragrance |
| (4) | 0.16 | Methyl chloroisothiazolinone / methylisothozolinone |

* 21.86% Dimethicone PEG-8 Polyacrylate (Momentive Performance Materials)
** 40% Acrylates / Dimethicone Copolymer in trimethicone (Shin-Etsu Chem. Co.)

separately mix phase 1 and phase 2, heating to 60° C.;
add phase 1 to phase 2 to while mixing at 60° C.;
add phase 3 at 40° C., with agitation;
at T<40° C., add phase 4;
allow to cool to room temperature For easiest formulating, it is preferable if the dimethicone PEG-8 polyacrylate is added to the formulation between 40° C. and 60° C.

Compositions described herein comprise acrylates/dimethicone copolymer and dimethicone PEG-8 polyacrylate in a cosmetically acceptable aqueous base or hydro/alcoholic base. In preferred compositions, acrylates/dimethicone copolymer and dimethicone PEG-8 polyacrylate are the sole or main hair styling agents in the aqueous composition. Water may be present in a wide range of concentration typical of hair care products, 40-98 wt. %, for example. Preferably, the concentration of water is 40-95 wt. %, more preferably 50-95 wt. %.

Compositions of the invention may, in general, include any cosmetically acceptable ingredients that are soluble, or at least dispersible, in the base, and that do not interfere with the substantivity of the hair for acrylates/dimethicone copolymer and dimethicone PEG-8 polyacrylate. Thus, any ingredient or treatment that would prevent a sufficient amount of for acrylates/dimethicone copolymer and dimethicone PEG-8 polyacrylate from remaining on the hair after a water rinse, are excluded from compositions and methods of the present invention.

In general, compositions of the invention may comprise one or more hair benefit agents, such as antidandruff agents, antimicrobial agents, antioxidants, cleansing agents, hair colorants, hair conditioning agents, moisturizers and sunscreens. Other ingredients may typically include, pH adjusters, viscosity controlling agents, surfactants, preservatives and propellants.

Conventional shampoo compositions comprise at least one primary surfactant, at least one secondary or co-surfactant and at least one foam boosting and/or foam stabilizing agent. At least one thickening and/or gelling agent, at least one pH adjuster, and at least one preservative are also common in shampoo. The primary surfactant provides cleansing and foaming. Typical concentrations of primary surfactant include 10%-35% by weight of the composition. Sulfates and sulfonates are two well known classes of primary shampoo surfactants, which include ammonium lauryl sulfate and alkyl sulfonate. Typical concentrations of secondary surfactants in shampoo compositions include 1%-20% by weight of the composition. Betaines and sulfosuccinates are two well known classes of secondary shampoo surfactants, which include cocobetaine and sulfosuccinate. Polyglucose is another common secondary surfactant in shampoos. Examples of foam boosting agents useful in shampoo compositions of the invention include cocamide MIPA, sodium laureth sulfate, ammonium lauryl sulfate, sarcosinates (such as sodium lauryl sarcosinate) and lactylates. Typical concentrations of foam boosting and/or foam stabilizing agents include 0.1%-10% by weight of the composition. One or more thickening agents may typically comprise 0.1% to 5% by weight of the composition. Non-limiting classes of thickening agents include those selected from the following: carboxylic acid polymers (such as carbomers, and acrylates/C10-C30 alkyl acrylate cross polymers); crosslinked polyacrylate polymers, polyacrylamide polymers (such as polyacrylamide (and) isoparaffin (and) laureth-7); multi-block copolymers of acrylamides and substituted acrylamides with acrylic acids and substituted acrylic acids; polysaccharides (including cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, alkyl substituted celluloses); gums (including acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum), and mixtures thereof. Examples of pH adjusters might include one or more the following: acetic acid, aminomethyl propanediol, ammonium bicarbonate, ammonium hydroxide, boric acid, calcium chloride, calcium hydroxide, citric acid, diisopropanolamine, dipotassium phosphate, glycine, isopropanolamine, L-Arginine, magnesium hydroxide, malic acid, pentasodium triphosphate, potassium bicarbonate, potassium hydroxide, potassium phosphate monobasic, sodium bicarbonate, sodium borate, sodium carbonate, sodium citrate, sodium hydroxide, sodium phosphate, sodium, triethanolamine, triisopropanolamine, trisodium phosphate, vinegar. Shampoo pH may typically be adjusted to be in the range 4.5-6.5. Preservatives (for example, methyl chloroisothiazolinone/methylisothozolinone and phenoxyethanol) may typically comprise up to 2% of the shampoo composition by weight. All of the foregoing shampoo ingredients and concentrations are give an as examples only, and many other ingredients and concentrations are known to be useful in shampoo compositions.

It is also possible to include other styling agents in compositions according to the invention. In that case, it should be possible to formulate an effective hold product with lesser concentrations of conventional styling agents. Also, in that case, the acrylates/dimethicone copolymer and dimethicone PEG-8 polyacrylate may be useful at concentrations below those specified above.

Also, although we have demonstrated that excellent hold and aesthetics may be achieved with rinse-out type products, the principles of the present invention may also be utilized in leave-in type products, such as hair styling gels and mousses, lotions and sprays. For leave-in products, the concentrations of Dimethicone PEG-8 Polyacrylate and Acrylates/Dimethicone Copolymer in the product may be lower than as specified above, due to the fact that all of the product that is applied to the hair remains in the hair (i.e. it is not rinsed away).

Compositions according to the invention are used in conjunction with a heat styling tool, such as a curling iron or blow dryer and brush. A typical method of using a composition according to the invention includes applying to a tress of hair enough of the composition to coat the hairs (for example, at least 0.1 g of the composition to each 3 g of hair being styled); working the composition throughout the tress so that the composition contacts most of the hairs being treated; rinsing the tress with water to remove excess composition from the hair; and heat styling the hair to impart one or more curls to the tress. A method of using a shampoo composition according to the invention includes wetting the head of hair to be styled; applying at least 0.5 g of the shampoo to each 10 g of hair being styled; lathering the shampoo into a foam throughout the head of hair; rinsing the hair with water to remove excess shampoo from the hair; and heat styling the hair to impart one or more curls to the head of hair.

What we claim is:

1. A topical hair styling composition comprising:
   a cosmetically acceptable base having 40%-98% water;
   0.5 to 5 wt. % acrylates/dimethicone copolymer;
   0.1 to 1 wt. % dimethicone PEG-8 polyacrylate;
   wherein the ratio of acrylates/dimethicone copolymer to dimethicone PEG-8 polyacrylate is 2:1 to 23:1.

2. The composition of claim 1 wherein the acrylates/dimethicone copolymer comprises 15,000-30,000 Da of acrylate and 15,000±20% Da of silicone.

3. The composition of claim 2 wherein the ratio of acrylates/dimethicone copolymer to dimethicone PEG-8 polyacrylate is 4:1 to 18:1.

4. The composition of claim 3 wherein the ratio of acrylates/dimethicone copolymer to dimethicone PEG-8 polyacrylate is 6:1 to 9:1.

5. A composition according to claim 1 wherein the composition is a shampoo composition further comprising:
   10-35% by weight of at least one primary surfactant;
   1-20% by weight of at least one co-surfactant;
   0.1%-10% by weight of at least one foam boosting agent; and
   0.1% to 5% by weight of at least one thickener.

6. A method for curling or styling a tress of hair comprising the steps of:
   providing a composition according to claim 1;
   applying at least 0.1 g of the composition to each 3 g of hair being styled;
   working the composition throughout the tress so that the composition contacts most of the hairs being treated;
   rinsing the tress with water to remove excess composition from the hair; and
   heat styling the hair to impart one or more curls to the tress.

7. A method for curling or styling a head of hair comprising the steps of:
   providing a shampoo composition according to claim 5;
   wetting the head of hair to be styled;
   applying at least 0.5 g of the shampoo to each 10 g of hair being styled;
   lathering the shampoo into a foam throughout the head of hair;
   rinsing the hair with water to remove excess shampoo from the hair; and
   heat styling the hair to impart one or more curls to the head of hair.

* * * * *